(12) United States Patent
Murakami

(10) Patent No.: US 6,717,020 B2
(45) Date of Patent: Apr. 6, 2004

(54) METHOD OF PRODUCING P-HYDROXYPHENYLALKANOLS

(75) Inventor: Chikara Murakami, Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/397,351

(22) Filed: Mar. 27, 2003

(65) Prior Publication Data

US 2003/0195379 A1 Oct. 16, 2003

(30) Foreign Application Priority Data

Mar. 29, 2002 (JP) .................................. 2002-094483
Mar. 29, 2002 (JP) .................................. 2002-094484

(51) Int. Cl.$^7$ .............................................. C07C 37/00
(52) U.S. Cl. ...................................... 568/766; 568/763
(58) Field of Search .................................. 568/766, 763

(56) References Cited

FOREIGN PATENT DOCUMENTS

| EP | 0 823 435 A2 | 2/1998 |
| JP | 2001-64220 A | 3/2001 |
| SU | 1814807 A3 | 1/1995 |

OTHER PUBLICATIONS

Derwent Publications Ltd., (XP002245665), Japanese Patent Application No. 2001–64220, published Mar. 13, 2001.
Derwent Publications Ltd., (XP002245666), Japanese Patent Application No. 2–221240, published Sep. 4, 1990.

*Primary Examiner*—Michael L. Shippen
(74) *Attorney, Agent, or Firm*—Sughrue Mion, PLLC

(57) ABSTRACT

Disclosed are a method of producing p-hydroxyphenylalkanol of formula(I):

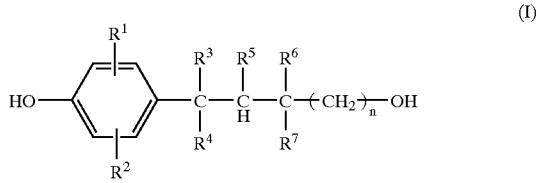

wherein $R^1$ and $R^2$ independently represent hydrogen, an alkyl or a phenyl which may be substituted with an alkyl, or the like, $R^3$, $R^4$, $R^5$, $R^6$ and $R^7$ independently represent hydrogen, an alkyl or the like and n denotes an integer from 0 to 7, the method being characterized in that a phenol compound of formula (II):

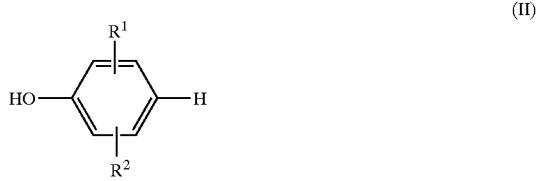

wherein $R^1$ and $R^2$ respectively represent the aforementioned meaning, is reacted with an unsaturated alcohol of formula (III):

$$R^3R^4C=C(R^5)-C(R^6)(R^7)-(CH_2)_n-OH \quad \text{(III)}$$

wherein $R^3$, $R^4$, $R^5$, $R^6$, $R^7$ and n respectively represent the same as defined above, in the presence of (A) at least one compound selected from the group consisting of alkali metals, alkali metal compounds, alkaline earth metals and alkaline earth metal compounds and (B) at least one compound selected from the group consisting of transition metals and transition metal compounds, and the like.

20 Claims, No Drawings

METHOD OF PRODUCING P-HYDROXYPHENYLALKANOLS

BACKGROUND OF THE INVENTION

1. Field of the Invention

The present invention relates to a method of producing p-hydroxyphenylalkanols.

2. Background of the Invention p-Hydroxyphenylalkanols are useful compounds as raw compounds for producing stabilizers for thermoplastic resins, raw compounds of pharmaceuticals and the like.

As a method of producing p-hydroxyphenylalkanols of the following formula:

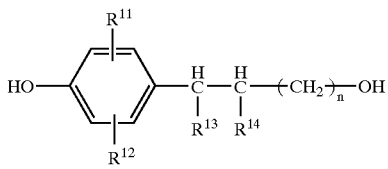

wherein $R^{11}$ and $R^{12}$ independently represent a hydrogen atom, an C1–8 alkyl group, a C5–8 cycloalkyl group, an C6–12 alkylcycloalkyl group, an C7–12 aralkyl group which may be substituted with an C1–8 alkyl group, a phenyl group which may be substituted with a C1–8 alkyl group, $R^{13}$ and $R^{14}$ independently represent a hydrogen atom or an C1–8 alkyl group, and n denotes an integer from 0 to 7, a method is known in which phenols represented by the following formula:

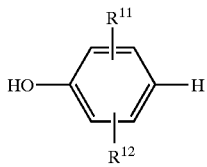

wherein $R^{11}$ and $R^{12}$ respectively represent the aforementioned meaning, are reacted with unsaturated alcohols represented by the following formula:

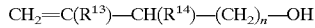

$$CH_2=C(R^{13})-CH(R^{14})-(CH_2)_n-OH$$

wherein $R^{13}$, $R^{14}$ and n respectively represent the same meaning as above, in the presence of a base (Japanese Patent Application Laid-Open (JP-A) No. 2001-64220). The aforementioned method, however, has a problem in that the reactivity is not satisfactory under a relatively mild reaction condition whereas the amount of by-produced impurities increases under a relatively severe condition, hence the yield of p-hydroxyphenylalkanols is not always satisfactory.

SUMMARY OF THE INVENTION

According to the present invention, p-hydroxyphenylalkanols of the following formula (I) can be produced in a good yield.

The present invention provides: as the first aspect of the invention, 1. a method for producing a p-hydroxyphenylalkanol of formula (I):

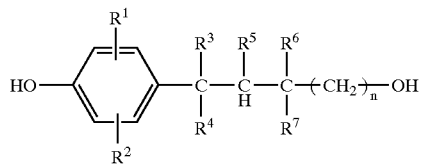

wherein $R^1$ and $R^2$ independently represent
  a hydrogen atom,
  an C1–8 alkyl group,
  an C1–8 alkoxy group,
  a C5–8 cycloalkyl group,
  an C6–12 alkylcycloalkyl group,
  an C7–12 aralkyl group which may be substituted with an C1–8 alkyl group,
  a phenyl group which may be substituted with a C1–8 alkyl group,
  a phenoxy group which may be substituted with a C1–8 alkyl group,
  $R^3$, $R^4$, $R^5$, $R^6$ and $R^7$ independently represent a hydrogen atom or an C1–8 alkyl group, and
  n denotes an integer from 0 to 7, which method comprises reacting a phenol compound of formula (II):

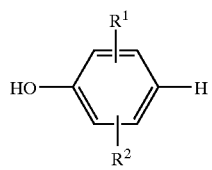

wherein $R^1$ and $R^2$ respectively represent the same as defined above, with an unsaturated alcohol of formula (III):

$$R^3R^4C=C(R^5)-C(R^6)(R^7)-(CH_2)_n-OH \quad (III)$$

wherein $R^3$, $R^4$, $R^5$, $R^6$, $R^7$ and n respectively represent the same as defined, in the presence of (A) at least one compound selected from the group consisting of an alkali metal, an alkali metal compound, an alkaline earth metal and an alkaline earth metal compound, and (B) at least one compound selected from the group consisting of a transition metal and a transition metal compound; and as the second aspect of the invention, 2. a method for producing a p-hydroxyphenylalkanol of formula (I) as defined above, which method comprises reacting the phenol compound of formula (II) as defined above with the unsaturated alcohol of formula (III) as defined above, in the presence of (a) an alkali metal or an alkali metal compound, and (b) an alkaline earth metal or an alkaline earth metal compound.

DETAILED DESCRIPTION OF THE INVENTION

A description will be made to the first aspect of the invention.

Examples of the C1–8 alkyl group represented by $R^1$ or $R^2$ include, for example, methyl, ethyl, n-propyl, i-propyl, n-butyl, i-butyl, sec-butyl, t-butyl, t-pentyl, n-hexyl, n-heptyl, i-octyl, t-octyl and 2-ethylhexyl groups.

Examples of the C1–8 alkoxy group represented by $R^1$ or $R^2$ include, for example, methoxy, ethoxy, n-propoxy, i-propoxy, n-butyloxy, i-butyloxy, sec-butyloxy, t-butyloxy, t-pentyloxy, n-hexyloxy, n-heptyloxy, i-octyloxy, t-octyloxy and 2-ethylhexyloxy groups.

Examples of the C5–8 cycloalkyl group by $R^1$ or $R^2$ include, for example, cyclopentyl, cyclohexyl, cycloheptyl and cyclooctyl groups.

Examples of the C6–12 alkylcycloalkyl group represented by $R^1$ or $R^2$ include, for example, 1-methylcyclopentyl, 1-methylcyclohexyl and 1-methyl-4-i-propylcyclohexyl groups.

Examples of the C7–12 aralkyl group which may be substituted with a C1–8 alkyl group represented by $R^1$ or $R^2$ include, for example, benzyl, phenylethyl, α-methylbenzyl and α, α-dimethylbenzyl.

Examples of the phenyl group which may be substituted with the C1–8 alkyl group represented by $R^1$ or $R^2$ include, for example, a phenyl group, methylphenyl, ethylphenyl, n-propylphenyl, i-propylphenyl, n-butylphenyl, i-butylphenyl, sec-butylphenyl, t-butylphenyl, t-pentylphenyl, n-hexylphenyl, n-heptylphenyl, i-octylphenyl, t-octylphenyl and 2-ethylhexylphenyl groups.

Examples of the phenoxy group which may be substituted with the C1–8 alkyl group represented by $R^1$ or $R^2$ include, for example, a phenoxy group, methylphenoxy, ethylphenoxy, n-propylphenoxy, i-propylphenoxy, n-butylphenoxy, i-butylphenoxy, sec-butylphenoxy, t-butylphenoxy, t-pentylphenoxy, n-hexylphenoxy, n-heptylphenoxy, i-octylphenoxy, t-octylphenoxy and 2-ethylhexylphenoxy, 2,6-di-t-butylphenoxy, 2,4-dimethyl-6-t-butylphenoxy groups.

At least one of $R^1$ and $R^2$ is preferably the C1–8 alkyl, C1–8 alkoxy, or C5–8 cycloalkyl group, the phenyl group which may be substituted with a C1–8 alkyl group, or the phenoxy group which may be substituted with a C1–8 alkyl group, more preferably an C1–8 alkyl group or a C5–8 cycloalkyl group and particularly preferably a methyl group or a t-alkyl group such as t-butyl, t-pentyl or t-octyl.

Examples of the phenol compound (II) include, for example, phenol, 2-methylphenol, 2-methoxyphenol, 2-t-butylphenol, 2-t-butoxyphenol, 2-t-pentylphenol, 2-t-pentyloxyphenol, 2-octylphenol, 2-cyclohexylphenol, 2-(1-methylcyclohexyl)phenol, 2,6-dimethylphenol, 2,6-dimethoxyphenol, 2-t-butyl-6-methylphenol, 2-t-butoxy-6-methylphenol, 2-t-butyl-6-methoxyphenol, 2-t-pentyl-6-methylphenol, 2-t-octyl-6-methylphenol, 2-cyclohexyl-6-methylphenol, 2-di-t-butoxyphenol, 2-(1-methylcyclohexyl)-6-methylphenol, 2-t-butyl-6-ethylphenol, 2-t-butyl-6-ethoxyphenol, 2-t-pentyl-6-ethylphenol, 2-t-octyl-6-ethylphenol, 2-cyclohexyl-6-ethylphenol, 2-(1-methylcyclohexyl)-6-ethylphenol, 2,6-di-t-butylphenol, 2-t-pentyl-6-t-butylphenol, 2,6-di-t-pentylphenol, 2-t-octyl-6-butylphenol, 2-cyclohexyl-6-t-butylphenol, 2-(1-methylcyclohexyl)-6-t-butylphenol, 2-phenyl-6-methylphenol, 2-phenyl-6-t-butylphenol, 2-tolyl-6-methylphenol, 2-tolyl-6-t-butylphenol, 2,6-diphenylphenol, 2-phenoxyphenol, 2-(2-methylphenoxy)phenol, 2-phenoxy-6-methylphenol, 2-phenoxy-6-t-butylphenol, 2-phenoxy-6-methoxyphenol, 2,6-diphenoxyphenol, 2-(2-methyl-6-t-butylphenoxy)phenol, 2-(2,4-dimethyl-6-t-butylphenoxy)phenol, 2-(2-methyl-6-t-butylphenoxy)-6-methylphenol, and 2-(2,4-dimethyl-6-t-butylphenoxy)-6-methylphenol.

Among these phenol compounds, 2-methyl-6-t-butylphenol or 2,6-di-t-butylphenol is preferably used.

Examples of the C1–8 alkyl group represented by $R^3$, $R^4$, $R^5$, $R^6$ or $R^7$ in the unsaturated alcohol of formula (III) include, for example, methyl, ethyl, n-propyl, i-propyl, n-butyl, i-butyl, sec-butyl, t-butyl, t-pentyl, n-hexyl, n-heptyl, i-octyl, t-octy, 2-ethylhexyl and the like. $R^3$ and $R^4$ are preferably hydrogen atoms.

Examples of the unsaturated alcohol (III) include, for example, allyl alcohol, 2-butene-1-ol, 3-butene-1-ol, 3-butene-2-ol, 2-methyl-2-propene-1-ol, 2-methyl-3-butene-1-ol, 3-methyl-2-butene-1-ol, 2-methyl-3-butene-2-ol, 3-methyl-3-butene-1-ol, 4-pentene-1-ol, 4-penetene-2-ol, 1-pentene-3-ol, 1-hexene-3-ol, 5-hexene-1-ol, 6-heptene-1-ol, 7-octene-1-ol, 8-nonene-1-ol or 9-decene-1-ol. Among these compounds, allyl alcohol is preferably used.

The amount of the unsaturated alcohol (III) that may be suitably used is usually about 0.1 to 10 moles and preferably about 1 to 5 moles per mol of the phenol compound (II).

Examples of the alkali metal include lithium, sodium and potassium.

Examples of the alkali metal compound include, for example, hydroxides, hydrides, carbonates, alkoxide and amides of alkali metals(e.g., lithium, sodium and potassium);

an alkali metal compound of formula (IV):

R—$M_a$ (IV)

wherein R represents an aliphatic or aromatic hydrocarbon group and $M_a$ represents the alkali metal atom; and aryloxides of formula (V):

ArO$M_a$ (V)

wherein $M_a$ represents the same as defined above, and Ar represents phenol residue, such as bisphenol A residue having two benzene nucleus, and monohydric, dihydric and trihydric phenol residue which may be substituted with an alkyl group or an alkoxy group.

Examples of the aliphatic or aromatic hydrocarbon group represented by R in the above formula (IV) include, for example, a methyl, ethyl, propyl, and butyl groups, phenyl and tolyl groups.

Specific examples of the hydroxides of alkali metals include, for example, lithium hydroxide, sodium hydroxide and potassium hydroxide.

Specific examples of the hydrides include, for example, sodium hydride and potassium hydride.

Specific examples of the alkali metal compound of formula (IV) include, for example, methyl lithium, butyl lithium, and phenyl lithium.

Specific examples of the carbonates include, for example, potassium carbonate, sodium carbonate, lithium carbonate and the like.

Specific examples of the amide include, for example, potassium amide, sodium amide, lithium amide and the like.

Specific examples of the alkali metal alkoxide include, for example, lithium methoxide, lithium ethoxide, lithium t-butoxide, sodium methoxide, sodium ethoxide, sodium t-butoxide, potassium methoxide, potassium ethoxide and potassium t-butoxide, and specific examples of the aryloxide of formula (V) include, for example, lithium phenoxide, sodium phenoxide, potassium phenoxide and the like.

Among these alkali metal compounds, preferred are alkali metal hydroxides such as lithium hydroxide, sodium hydroxide and potassium hydroxide, alkali metal alkoxides such as lithium methoxide, lithium ethoxide, lithium t-butoxide, sodium methoxide, sodium ethoxide, sodium t-butoxide, potassium methoxide, potassium ethoxide and potassium t-butoxide.

Examples of the alkaline earth metal include, for example, magnesium, calcium and barium.

Examples of the alkaline earth metal compound include, for example, hydroxides, hydrides, oxides, halides, carboxylates, alkoxides, amides and carbonates of alkaline earth metals (e.g. magnesium, calcium and barium); and an alkaline earth metal compound of formula (VI):

$$R-M_b-R' \quad (VI)$$

wherein R and R' independently represent an aliphatic or aromatic hydrocarbon group, and $M_b$ represents an alkaline earth metal atom (e.g. magnesium, calcium and barium);

an alkaline earth metal aryloxide of formula (VII):

$$ArOM_bOAr' \quad (VII)$$

wherein $M_b$ represents the same as defined above, and Ar and Ar' independently represent a phenol residue such as bisphenol A residue having two benzene nucleus, and monohydric, dihydric or trihydric phenol residue which may be substituted with an alkyl group or an alkoxy group; and a Grignard compound of formula (VIII):

$$R-Mg-X \quad (VIII)$$

wherein R represents the same as defined above and X represents a halogen atom (e.g. chlorine, bromine, and iodine).

Examples of the alkaline earth metal hyroxide include, for example, barium hydroxide, calcium hydroxide and the like.

Examples of the alkaline earth metal hydride include, for example, magnesium hydride and the like.

Examples of the alkaline earth metal oxide include, barium oxide, calcium oxide and the like.

Examples of the alkaline earth metal halide include, for example, magnesium chloride, magnesium bromide, and magnesium iodide and the like.

Examples of the alkaline earth metal carboxylates include, for example, magnesium acetate, barium acetate, calcium acetate and the like.

Examples of the alkaline earth metal amide include, for example, magnesium amide and the like.

Examples of the carbonates include, for example, magnesium carbonate, barium carbonate, calcium carbonate and the like.

Examples of the aliphatic or aromatic hydrocarbon group represented by R or R' in the above formulae (VI) or (VIII) include an alkyl group such as methyl, ethyl, propyl, or butyl group, and an aryl group such as phenyl group or tolyl group.

Examples of the alkaline earth metal compound of formula (VI) include, for example, dimethyl magnesium, diphenyl magnesium and the like.

Examples of the alkaline earth metal alkoxide include, for example, magnesium alkoxides such as magnesium methoxide, magnesium ethoxide, calcium ethoxide and barium ethoxide.

Examples of the aryloxide of formula (VII) include, for example, magnesium phenoxide and the like.

Examples of the Grignard compound of formula (VIII) include, methyl magnesium chloride, methyl magnesium bromide, methyl magnesium iodide, n-butyl magnesium chloride, sec-butyl magnesium chloride, t-butyl magnesium chloride, phenyl magnesium chloride and the like.

At least one compound selected from the group consisting of the alkali metal, alkali metal compound, the alkaline earth metal and alkaline earth metal compound is usually used in an amount of about 0.01 to 2 moles and more preferably about 0.05 to 1 mol per mol of the phenol compound (II).

Examples of the transition metal include, for example, iron or zinc.

Examples of the transition metal compound include, for example, hydroxides, oxides, halides, carbonates, hydrides, alkoxides, aryloxides and sulfides of transition metals, and alkylated transition metal compound such as diethyl zinc;

a divalent transition metal compound of formula (IX):

$$R-M_c-Y \quad (IX)$$

wherein R represents an alkyl group or an aryl group, Y represents an alkoxy group, an aryloxy group or a halogen atom and $M_c$ represents a divalent transition metal atom (e.g. methyl zinc iodide, phenyl zinc iodide, and the like); and a tetravalent transition metal compound of formula (X):

$$RR'M_dYZ \quad (X)$$

wherein R and R' independently represent the aliphatic or aromatic hydrocarbon group as defined above, Y and Z independently represent an alkoxy group, an aryloxy group or a halogen atom and $M_d$ represents a tetravalent transition metal atom (e.g. dimethyl titanium dichloride, dimethyl titanium diisopropoxide, dimethyl titanium diisopropoxide, bis (cyclopentyadienyl) titanium dichloride and the like).

Specific examples of these transition metal compounds include, for example, alkoxides such as titanium alkoxide (e.g. titanium tetramethoxide, titanium tetraethoxide, titanium tetraisopropoxide), zirconium tetrabutoxide, diethoxy zinc, hydroxides such as lanthanum hydroxide, hydrides such as titanium hydride, halides such as titanium tetrachloride, zirconium tetrachloride and zinc chloride, alkoxy halides such as dichlorodiisopropoxy titanium, oxides such as zinc oxide, sulfides such as titanium sulfide and a complex of transition metal halides such as cyclopentadienyldichlorotitanium. Preferred is titanium (IV) alkoxides.

The transition metal compound is usually used in an amount of about 0.01 to 2 moles and preferably about 0.05 to 1 mol per mol of the phenol compound (II).

In the present invention, the reaction is conducted in the presence or absence of a reaction solvent.

Examples of the reaction solvent include, for example, aromatic hydrocarbon solvents such as benzene, toluene, xylene, ethylbenzene, chlorobenzene and nitrobenzene, ether solvents such as diethyl ether, dibutyl ether, diisopropyl ether, tetrahydrofuran, dimethoxyethane or diglyme, and aliphatic hydrocarbon solvents such as n-hexane, n-heptane, cyclohexane, octane and decane, or alcohol solvents such as n-butyl alcohol, sec-butyl alcohol, t-butyl alcohol and diethylene glycol, and a mixture thereof.

The amount of the reaction solvent that may be suitably used is preferably about 0.1 to 5 parts by weight per 1 part by weight of the phenol compound (II).

In the present invention, there is no particular limitation as to the order of addition of at least one compound selected from the group consisting of alkali metals, alkali metal compounds, alkaline earth metals and alkaline earth metal compounds, and at least one compound selected from the group consisting of transition metals and transition metal compounds.

For example, (i) the phenol compound and the unsaturated alcohol may be simultaneously added into a reactor and reacted in the presence of at least one compound selected from the group consisting of alkali metals, alkali metal compounds, alkaline earth metals and alkaline earth metal compounds, and at least one compound selected from the group consisting of transition metals and transition metal compounds; or (ii) at least one compound selected from the group consisting of alkali metals, alkali metal compounds, alkaline earth metals and alkaline earth metal compounds and the phenol compound may be added to produce corresponding phenolate and then at least one compound selected from the group consisting of transition metals and transition metal compound and the unsaturated alcohol may be added to the produced phenolate to react the unsaturated alcohol with the phenolate; or (iii) at least one compound selected from the group consisting of alkali metals, alkali metal compounds, alkaline earth metals and alkaline earth metal compounds may be reacted with the unsaturated alcohols and then at least one compound selected from the group consisting of transition metals and transition metal compounds and the phenol compound are added to react the phenols with the resulting product.

In the case of (i) above, the reaction is usually conducted in a tightly closed system at a temperature, typically higher than the boiling point of the unsaturated alcohol. The reaction temperature is preferably about 100 to 300° C. and more preferably about 180 to 250° C.

In the case of (ii) above, at least one compound selected from the group consisting of alkali metals, alkali metal compounds, alkaline earth metals and alkaline earth metal compounds and the phenol compound are reacted at a reaction temperature ranging from room temperature to about 200° C. Water produced during the reaction using the hydroxide of an alkali metal or an alkaline earth metal may be removed from the reaction system. Alcohols produced during the reaction using the alkoxide of an alkali metal or alkali earth metal may be removed from the reaction system.

After water and these alcohols are removed, at least one compound selected from the group consisting of transition metals and transition metal compounds and the unsaturated alcohols (III) are added to the above reaction mixture and usually, the reaction is usually conducted in a tightly closed system at a temperature typically higher than the boiling point of the unsaturated alcohol. The reaction temperature is preferably about 100 to 300° C. and more preferably about 180 to 250° C.

In the case of (iii) above, the reaction is usually conducted in a tightly closed system at a temperature typically higher than the boiling point of the unsaturated alcohol. The reaction temperature is preferably about 100 to 300° C. and more preferably about 180 to 250° C.

The progress of the reaction in the present invention can be monitored using analytical means such as gaschromatography or liquid chromatography.

The p-hydroxyphenylalkanols (I) thus produced may be isolated or separated, for example, by adding an inorganic acid such as sulfuric acid and hydrochloric acid or an organic acid such as acetic acid and then by adding an organic solvent, if necessary, to extract or separate the p-hydroxyphenylalkanol (I) and thereafter the unreacted raw material and/or the organic solvent in the extract may be distilled. The p-hydroxyphenylalkanols (I) isolated or separated in this manner may be further purified by means such as distillation, crystallization or liquid column chromatography, if necessary. Unreacted phenol compound (II) or an unsaturated alcohol (III) may be recovered and reused.

Next, a description will be made to the second aspect of the invention drawn to a method of producing the p-hydroxyphenylalkanol of formula (I), which method comprises reacting the phenol compound of formula (II), with the unsaturated alcohol of formula (III), in the presence of (a) an alkali metal or an alkali metal compound, and
(b) an alkaline earth metal or an alkaline earth metal compound.

Examples of the alkali metal include, for example, lithium, sodium and potassium.

Examples of the alkali metal compound include, for example, hydroxides, hydrides, carbonates, amides aryloxides and alkoxides of these alkali metals, and an alkali metal compound of formula (IV) as defined above.

Examples of the aliphatic or aromatic hydrocarbon group represented by R in formula (IV) include, for example, ethyl, butyl, phenyl and tolyl groups.

Among the alkali metal compounds, preferred are an alkali metal alkoxide such as lithium methoxide, lithium ethoxide, lithium t-butoxide, sodium methoxide, sodium ethoxide, sodium t-butoxide, potassium methoxide, potassium ethoxide or potassium t-butoxide, and more preferred is sodium methoxide.

The alkali metal or the alkali metal compound is typically used in an amount of 0.01 to 2 moles, preferably 0.05 to 1 mol per mol of the phenol compound of formula (II).

Examples of the alkaline earth metal include, for example, magnesium, calcium, barium and the like. Preferred is magnesium.

Examples of the alkaline earth metal compound include, for example, the hydroxide, hydride, oxide, halide, amide, carbonate, carboxylate and alkoxide of alkaline earth metals as defined above, the alkaline earth metal compound of formula (VI) as defied above, the alkaline earth metal aryloxide of formula (VII) as defined above, and the Grignard compound of formula (VIII) as defined above.

Among the alkaline earth metal compounds, preferred are magnesium compounds such as hydroxide, oxide, halide, amide, carbonate, carboxylate or alkoxide of magnesium, an alkaline earth metal compound of formula (VI) wherein $M_b$ represents magnesium, an alkaline earth metal aryloxide of formula (VII) wherein $M_b$ represents magnesium, or the Grignard compound of formula (VIII), and more preferred are magnesium acetate, magnesium alkoxides such as magnesium methoxide or magnesium ethoxide, and alkaline earth metal compound of formula (VI) wherein $M_b$ is magnesium, and yet more preferred is magnesium alkoxides such as magnesium methoxide.

Specific examples of the combinations of (a) the alkali metal or the alkali metal compound, and (b) the alkaline earth metal or alkaline earth metal compound include, for example, a combination of sodium hydroxide and magnesium acetate,
a combination of sodium hydroxide and magnesium alkoxide such as magnesium methoxide,
a combination of sodium methoxide and magnesium oxide,
a combination of magnesium alkoxide (e.g. methoxide) and sodium alkoxide (e.g. methoxide), and the like.

The amount of the alkaline earth metal or alkaline earth metal compound that may be suitably used is preferably about 0.01 to 2 moles and more preferably about 0.02 to 1 mol per mol of the phenol compound (II).

The reaction is carried out in the presence or absence of a reaction solvent.

Examples of the reaction solvent include, the same solvent that may be suitably used for the first aspect of the invention above.

The amount of the reaction solvent that may be suitably used is preferably about 0.1 to 5 parts by weight per one part by weight of the phenol compound (II).

In the present invention, there is no particular limitation as to the order of addition of these compounds.

For example, (i) amixture of the alkali metal or the alkali metal compound and the alkaline earth metal or the alkaline earth metal compound, the phenol compound (II) and the unsaturated alcohol (III) may be fed simultaneously and reacted with each other, or (ii) the alkali metal or the alkali metal compound, and the alkaline earth metal or the alkaline earth metal compound and the phenol may be fed, then the unsaturated alcohol may be fed and the resulting mixture may be reacted, or (iii) one of the alkali metal or the alkali metal compound and the alkaline earth metal or the alkaline earth metal compound, and the unsaturated alcohol may be fed first and then the other of the alkali metal or the alkali metal compound and the alkaline earth metal or the alkaline earth metal compound and the phenol compound (II) may be fed and the mixture is reacted.

In the case of feeding the alkali metal or the alkali metal compound and the alkaline earth metal or the alkaline earth metal compound, the phenol compound (II) and the unsaturated alcohol (III) are fed simultaneously, and the reaction is usually carried out under tightly closed system at a temperature higher than the boiling point of the unsaturated alcohol. The reaction temperature is preferably about 100 to 300° C. and more preferably about 180 to 250° C.

In the case of feeding the alkali metal or the alkali metal compound and the alkaline earth metal or the alkaline earth metal compound and the phenol compound (II) and then feeding the unsaturated alcohol (III) to conduct a reaction, the alkali metal or the alkali metal compound and the alkaline earth metal or the alkaline earth metal compound are usually reacted with the phenol compound (II) at a temperature ranging from room temperature to about 200° C. Water produced during the reaction using the hydroxides of an alkali metal or alkaline earth metal may be removed from the reaction system. Alcohols produced during the reaction using the alkoxide of an alkali metal or alkali earth metal may be removed from the reaction system.

After these operations, the reaction mixture is usually closed tightly and the unsaturated alcohols (III) are fed to react usually at a temperature higher than the boiling point of the unsaturated alcohols. The reaction temperature is preferably about 150 to 300° C. and more preferably about 180 to 250° C.

The progress of the reaction in the present invention may be monitored by using analytical means such as gas-chromatography or liquid chromatography. After completion of the reaction, the resulting reaction mixture is treated as described above for the first aspect of the invention to isolate the desired compound.

Examples of the p-hydroxyphenylalkanol (I) that may be produced in the first aspect or the second aspect of the present invention include, for example,
3-(4-hydroxyphenyl)propanol,
4-(4-hydroxyphenyl)butane-2-ol,
3-(3-methyl-4-hydroxyphenyl)propanol,
3-(3-methoxy-4-hydroxyphenyl)propanol,
3-(3-t-butyl-4-hydroxyphenyl)propanol,
3-(3-t-butoxy-4-hydroxyphenyl)propanol,
3-(3-t-pentyl-4-hydroxyphenyl)propanol,
3-(3-t-octyl-4-hydroxyphenyl)propanol,
3-(3-cyclohexyl-4-hydroxyphenyl)propanol,
3-[3-(1-methylcyclohexyl)-4-hydroxyphenyl]propanol,
3-(3-phenyl-4-hydroxyphenyl)propanol,
3-(3-tolyl-4-hydroxyphenyl)propanol,
3-(3-phenoxy-4-hydroxyphenyl)propanol,
3-[3-(2-methylphenoxy)-4-hyrdoxyphenyl]propanol,
3-(3,5-dimethyl-4-hydroxyphenyl)propanol,
3-(3,5-dimethoxy-4-hydroxyphenyl)propanol,
3-(3-t-butyl-4-hydroxy-5-methylphenyl)propanol,
3-(3-t-butyl-4-hydroxy-5-methoxyphenyl)propanol,
3-(3-t-pentyl-4-hydroxy-5-methylphenyl)propanol,
3-(3-t-octyl-4-hydroxy-5-methylphenyl)propanol,
3-(3-cyclohexyl-4-hydroxy-5-methylphenyl)propanol,
3-[3-(1-methylcyclohexyl)-4-hydroxy-5-methylphenyl]propanol,
3-[3-(1-methylcyclohexyl)-4-hydroxy-5-methoxyphenyl]propanol, 3-(3-phenyl-4-hydroxy-5-methylphenyl)propanol,
3-(3-phenyl-4-hydroxy-5-methoxyphenyl)propanol,
3-(3-phenoxy-4-hydroxy-5-methylphenyl)propanol,
3-(3-phenoxy-4-hydroxy-5-methoxyphenyl)propanol,
3-(3-t-butyl-4-hydroxy-5-ethylphenyl)propanol,
3-(3-t-pentyl-4-hydroxy-5-ethylphenyl)propanol,
3-(3-t-octyl-4-hydroxy-5-ethylphenyl)propanol,
3-(3-cyclohexyl-4-hydroxy-5-ethylphenyl)propanol,
3-[3-(1-methylcyclohexyl)-4-hydroxy-5-ethylphenyl]propanol,
3-(3,5-di-t-butyl-4-hydroxyphenyl)propanol,
3-(3-t-pentyl-4-hydroxy-5-t-butylphenyl)propanol,
3-(3-phenyl-4-hydroxy-5-t-butylphenyl)propanol,
3-(3-tolyl-4-hydroxy-5-t-butylphenyl)propanol,
3-(3-phenoxy-4-hydroxy-5-t-butylphenyl)propanol,
3-[3-(2-methylphenoxy)-4-hydroxy-5-t-butylphenyl]propanol,
3-(3,5-di-t-pentyl-4-hydroxyphenyl)propanol,
3-(3-t-octyl-4-hydroxy-5-t-butylphenyl)propanol,
3-(3-cyclohexyl-4-hydroxy-5-t-butylphenyl)propanol and
3-[3-(1-methylcyclohexyl)-4-hydroxy-5-t-butylphenyl]propanol, 3-(3,5-diphenyl-4-hydroxyphenyl)propanol,
3-(3,5-ditolyl-4-hydroxyphenyl)propanol,
3-(3,5-diphenoxy-4-hydroxyphenyl)propanol, and
3-[3,5-di-(2-methylphenoxy)-4-hydroxy-phenyl]propanol.

EXAMPLES

The present invention will be explained in more detail by way of examples, which, however, are not to be construed to limit the present invention thereto.

Example 1

A pressure container was charged with 62.4 g (0.38 mol) of 2-methyl-6-t-butylphenol, 14.7 g (0.076 mol) of a methanol solution containing 28% sodium methoxide and 17.4 g (0.076 mol) of titanium tetraethoxide. The mixture was heated under reduced pressure to distill a mixture of 13.0 g (0.41 mol) of methanol and 14.1 g (0.31 mol) of ethanol out of the reaction system. Thereafter, 53.2 g (0.92 mol) of allyl alcohol and 38.7 g (0.42 mol) of toluene were added to the reaction system and the atmosphere in the reaction system was replaced by nitrogen. Then, the reaction system was tightly closed, heated up to 210° C. and kept at that temperature for 7 hours. Then, the reaction system was cooled to room temperature. A sample of the reaction solution was analyzed by gas-chromatography. The desied product, 3-(3-t-butyl-4-hydroxy-5-methylphenyl)propanol was obtained in a yield of 78%.

Example 2

After charging 5.2 g (0.027 mol) of 28% sodium methoxide in methanol and 10.6 (0.33 mol) of methanol into a reaction vessel, 0.67 g (0.027 mol) of magnesium was added thereto and heated under nitrogen atmosphere until methanol begun to reflux while removing 0.06g (0.027 mol) of hydrogen out of the reaction system. Evolution of hydrogen gas had ceased after maintaining the heating.

To the solution obtained above after hydrogen gas evolution had ceased, 45 g (0.27 mol) of 2-methyl-6-t-butylphenol were added, and then heated under reduced pressure, thereby 15 g (0.47 mol) of methanol were removed from the reaction system. Then, 15.9 g (0.27 mol) of allyl alcohol and 13.5 g (0.15 mol) of toluene were added thereto. The resulting solution after the addition of toluene and allyl alcohol were transferred to a pressure container, and the atmosphere thereof was substituted with nitrogen gas, sealed and heated up to 210° C. and maintained at the same temperature for 4 hours. Thereafter the reaction mixture was cooled to room temperature and a sample thereof was analyzed by gas-chromatography. The desired product, 3-(3-t-butyl-4-hydroxy-5-methylphenyl)propanol was obtained in a yield of 82%.

Example 3

After charging 23 g (0.14 mol) of 2-methyl-6-t-butylphenol in a reaction vessel A, 14 ml (0.03 mol) of butyl magnesium chloride in diethyl ether were added thereto.

After 23 g (0.14 mol) of 2-methyl-6-t-butylphenol were added into another reaction vessel B, 0.62 g (0.03 mol) of sodium was added thereto under nitrogen atmosphere.

The solutions in reaction vessels A and B obtained above were transferred into a pressure container respectively and mixed. Then 15.9 g (0.27 mol) of ally alcohol were added thereto. The atmosphere of the reaction container were replaced with nitrogen and sealed and heated to 210° C., and maintained at the same temperature for 4 hours. Then, the reaction mixture was cooled to room temperature and a sample of the reaction solution was analyzed by gas-chromatography. The desired product, 3-(3-t-butyl-4-hydroxy-5-methylphenyl)propanol was obtained in a yield of 80%.

Example 4

A pressure container was charged with 62.4 g (0.38 mol) of 2-methyl-6-t-butylphenol, 7.3 g (0.038 mol) of a methanol solution containing 28% of sodium methoxide and 4.35 g (0.038 mol) of magnesium ethoxide. The mixture was heated under reduced pressure to distill a mixture of 6.5 g (0.2 mol) of methanol and 3.5 g (0.075 mol) of ethanol out of the reaction system. Thereafter, 22.2 g (0.38 mol) of allyl alcohol and 18.7 g (0.19 mol) of toluene were added to the reaction system and the atmosphere in the reaction system was replaced by nitrogen. Then, the reaction system was tightly closed, raised up to 210° C. and kept at that temperature for 7 hours. Then, the reaction mixture was cooled to room temperature. A part of the reaction solution was sampled and analyzed by gas-chromatography. The yield of 3-(3-t-butyl-4-hydroxy-5-methylphenyl)propanol which was the target compound was 78%.

Comparative Example 1

A pressure container was charged with 62.7 g (0.38 mol) of 2-methyl-6-t-butylphenol and 7.3 g (0.038 mol) of a methanol solution containing 28% of sodium methoxide. Then the mixture was heated under reduced pressure to distill 6.5 g (0.2 mol) of methanol. Thereafter, 22.2 g (0.92 mol) of allyl alcohol and 18.7 g (0.19 mol) of toluene were added to the reaction system, the atmosphere in the reaction system was replaced by nitrogen and then, the reaction system was tightly closed. Then, the reaction system was raised up to 210° C. and kept at that temperature for 7 hours. Then, the reaction mixture was cooled to room temperature. A sample of the reaction solution was analyzed by gas-chromatography. The desired product, 3-(3-t-butyl-4-hydroxy-5-methylphenyl)propanol was obtained in a yield of 52%.

According to the present invention, p-hydroxyphenylalkanol (I) are obtained in a good yield. Also, when a thermoplastic resin stabilizer is produced by using the phenylalkanol (I) obtained by the method of the present invention as a raw compound, the amount of impurities in the stabilizer can be decreased to less than tolerable level.

What is claimed is:

1. A method for producing a p-hydroxyphenylalkanol of formula (I):

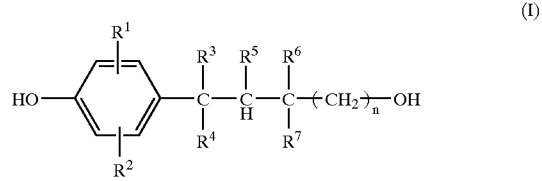

wherein $R^1$ and $R^2$ independently represent a hydrogen atom, an C1–8 alkyl group, an C1–8 alkoxy group, a C5–8 cycloalkyl group, an C6–12 alkylcycloalkyl group, an C7–12 aralkyl group which may be substituted with an C1–8 alkyl group, a phenyl group which may be substituted with a C1–8 alkyl group, a phenoxy group which may be substituted with a C1–8 alkyl group, $R^3$, $R^4$, $R^5$, $R^6$ and $R^7$ independently represent a hydrogen atom or an C1–8 alkyl group, and n denotes an integer from 0 to 7, which method comprises reacting a phenol compound of formula (II):

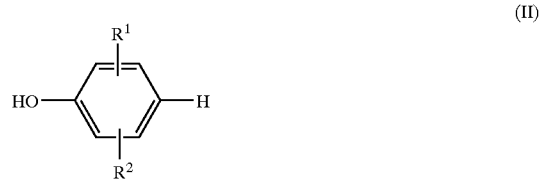

wherein $R^1$ and $R^2$ respectively represent the same as defined above, with an unsaturated alcohol of formula (III):

wherein $R^3$, $R^4$, $R^5$, $R^6$, $R^7$ and n respectively represent the same as defined above, in the presence of (A) at least one compound selected from the group consisting of an alkali metal, an alkali metal compound, an alkaline earth metal and an alkaline earth metal compound, and (B) at least one compound selected from the group consisting of a transition metal and a transition metal compound.

2. A method according to claim 1, wherein at least one of $R^1$ and $R^2$ in the phenol compound (I) is an C1–8 alkyl group, an C1–8 alkoxy group, a C5–8 cycloalkyl group, a phenyl group which may be substituted with a C1–8 alkyl group, or a phenoxy group which may be substituted with a C1–8 alkyl group.

3. A method according to claim 1 or 2, wherein the unsaturated alcohol (III) is allyl alcohol.

4. A method according to claim 1, wherein the phenol compound (II) is at least one compound selected from 2-methyl-6-t-butylphenol and 2,6-di-t-butylphenol.

5. A method according to claim 1, wherein the alkali metal compound is hydroxides, hydrides, carbonates, amides or alkoxides of the alkali metal, an alkali metal compound of formula (IV):

R—$M_a$ (IV)

wherein R represents an aliphatic or aromatic hydrocarbon group and $M_a$ represents the alkali metal atom; or an aryloxide of alkali metal of formula (V):

ArO$M_a$ (V)

wherein $M_a$ represents the same as defined above, and Ar represents a phenol residue;

the alkaline earth metal compound is hydroxide, hydride, oxide, halide, carboxylate, alkoxide, amide or carbonate of the alkaline earth metal;

an alkaline earth metal compound of formula (VI):

R—$M_b$—R' (VI)

wherein R and R' independently represent an aliphatic or aromatic hydrocarbon group, and $M_b$ represents an alkaline earth metal atom, an alkaline earth metal aryloxide of formula (VII):

ArO$M_b$OAr' (VII)

wherein $M_b$ represents the same as defined above, and Ar and Ar' independently represent a phenol residue, or a Grignard compound of formula (VIII):

R—Mg—X (VIII)

wherein R represents the same as defined above and X represents a halogen atom.

6. A method according to claim 5, wherein the alkali metal compound is alkali metal hydroxide or alkali metal alkoxide.

7. A method according to claim 5, wherein the transition metal is iron or zinc.

8. A method according to claim 1, wherein the transition metal compound is at least one compound selected from a hydroxide, oxide, halide, carbonate, alkoxide and phenoxide of a transition metal, a compound of formula (IX):

R—$M_c$—Y (IX)

wherein R represents an alkyl group or an aryl group, Y represents an alkoxy group, an aryloxy group or a halogen atom and $M_c$ represents a divalent transition metal atom, and a compound of formula (X):

RR'$M_d$YZ (X)

wherein R and R' independently represent an alkyl group or an aryl group, Y and Z independently represent an alkoxy group, an aryloxy group or a halogen atom and $M_d$ represents a tetravalent transition metal atom.

9. A method according to claim 8, wherein the alkaline earth metal compound is titanium (IV) alkoxide.

10. A method according to claim 1, wherein the reaction temperature is in a range from 100 to 300° C.

11. A method for producing a p-hydroxyphenylalkanol of formula (I):

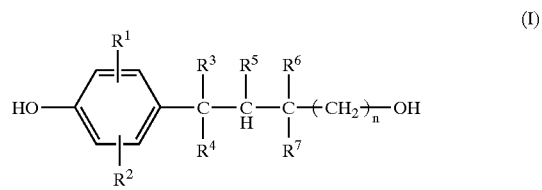

(I)

wherein $R^1$ and $R^2$ independently represent a hydrogen atom, an C1–8 alkyl group, an C1–8 alkoxy group, a C5–8 cycloalkyl group, an C6–12 alkylcycloalkyl group, an C7–12 aralkyl group which may be substituted with an C1–8 alkyl group, or a phenyl group which may be substituted with an C1–8 alkyl group, a phenoxy group which maybe substituted with an C1–8 alkyl group, $R^3$, $R^4$, $R^5$, $R^6$ and $R^7$ independently represent a hydrogen atom or an C1–8 alkyl group, and n denotes an integer from 0 to 7, which method comprises reacting a phenol compound of formula (II):

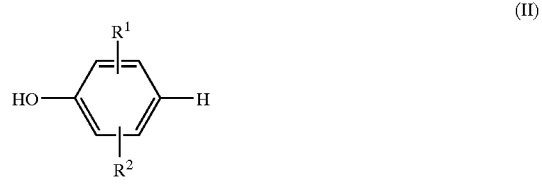

(II)

wherein $R^1$ and $R^2$ independently represent the same as defined above, with an unsaturated alcohol of formula (III):

$R^3R^4C=C(R^5)—C(R^6)(R^7)—(CH_2)_n—OH$ (III)

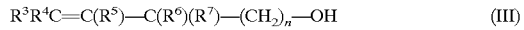

wherein $R^3$, $R^4$, $R^5$, $R^6$, $R^7$ and n independently represent the same as defined above, in the presence of (a) an alkali metal or an alkali metal compound, and (b) an alkaline earth metal or an alkaline earth metal compound.

12. A method according to claim 11, wherein at least one of $R^1$ and $R^2$ in the phenol compound (II) is an C1–8 alkyl group, an C1–8 alkoxy group, a C5–8 cycloalkyl group, a phenyl group which may be substituted with a C1–8 alkyl group, or a phenoxy group which may be substituted with a C1–8 alkyl group.

13. A method according to claim 11 or 12, wherein the unsaturated alcohol (III) is allyl alcohol.

14. A method according to claim 11, wherein the phenol (II) is at least one compound selected from 2-methyl-6-t-butylphenol and 2,6-di-t-butylphenol.

15. A method according to claim 11, wherein the alkali metal compound is at least one selected from hydroxide, hydride, carbonate, amide and alkoxide of an alkali metal, an alkali metal compound of formula (IV):

$$R—M_a \tag{IV}$$

wherein R represents an aliphatic or aromatic hydrocarbon group and $M_a$ represents an alkali metal atom;

an aryloxide of alkali metal of formula (V):

$$ArOM_a \tag{V}$$

wherein $M_a$ represents the same as defined above, and Ar represents a phenol residue.

16. A method according to claim 11, wherein the alkaline earth metal compound is at least one compound selected from hydroxide, hydride, oxide, halide, carboxylate, alkoxide, amide and carbonate of alkaline earth metal; and an alkaline earth metal compound of formula (VI):

$$R—M_b—R' \tag{VI}$$

wherein R and R' independently represent an aliphatic or aromatic hydrocarbon group, and $M_b$ represents an alkaline earth metal atom;

an alkaline earth metal aryloxide of formula (VII):

$$ArOM_bOAr' \tag{VII}$$

wherein $M_b$ represents the same as defined above, and Ar and Ar' independently represent a phenol residue; and a Grignard compound of formula (VIII):

$$R—Mg—X \tag{VIII}$$

wherein R represents the same as defined above and X represents a halogen atom.

17. A method according to claim 16, wherein the alkaline earth metal compound is the hydroxide, hydride, or alkoxide of the alkaline earth metal or the alkaline earth metal compound of formula (VI).

18. A method according to claim 17, wherein the alkali metal compound is an alkali metal alkoxide and the alkaline earth metal compound is an alkaline earth metal alkoxide.

19. A method according to claim 11, wherein the reaction temperature is in the range from 100 to 300° C.

20. A method according to claim 11, wherein the alkaline earth metal in the alkaline earth metal or the alkaline earth metal compound is magnesium.

* * * * *